United States Patent
Poston

(10) Patent No.: US 10,440,956 B2
(45) Date of Patent: Oct. 15, 2019

(54) PIPE FITTING ADHESIVE COMPOUND WITH VEGETATION DETERRING PROPERTIES

(71) Applicant: T. Christy Enterprises, Inc., Anaheim (CA)

(72) Inventor: Laura L. Poston, Laguna Niguel, CA (US)

(73) Assignee: T. Christy Enterprises, Inc., Anaheim, CA (US)

( * ) Notice: Subject to any disclaimer, the term of this patent is extended or adjusted under 35 U.S.C. 154(b) by 734 days.

(21) Appl. No.: 14/938,522

(22) Filed: Nov. 11, 2015

(65) Prior Publication Data

US 2016/0128334 A1 May 12, 2016

Related U.S. Application Data

(60) Provisional application No. 62/078,812, filed on Nov. 12, 2014.

(51) Int. Cl.
| | |
|---|---|
| *A01N 59/16* | (2006.01) |
| *A01N 59/20* | (2006.01) |
| *C09J 9/00* | (2006.01) |
| *C09J 11/04* | (2006.01) |

(Continued)

(52) U.S. Cl.
CPC ............. *A01N 59/16* (2013.01); *A01N 59/20* (2013.01); *C09J 9/00* (2013.01); *C09J 11/04* (2013.01); *C09J 121/00* (2013.01); *F16L 1/11* (2013.01); *F16L 57/00* (2013.01); *F16L 58/1054* (2013.01); *C08K 3/015* (2018.01); *C08K 3/08* (2013.01); *C08K 3/22* (2013.01);

(Continued)

(58) Field of Classification Search
CPC ........ C09J 11/04; C09J 121/00; C09J 121/02; C09J 107/00; C09J 107/02; A01N 59/20
See application file for complete search history.

(56) References Cited

U.S. PATENT DOCUMENTS

| | | | |
|---|---|---|---|
| 4,647,072 A | 3/1987 | Westman | |
| 4,814,227 A * | 3/1989 | Maeda | ..................... B63B 59/04 428/353 |

(Continued)

FOREIGN PATENT DOCUMENTS

| | | | | |
|---|---|---|---|---|
| CN | 101942891 A | * | 1/2011 | |
| GB | 2333772 A | * | 8/1999 | ............... A61K 8/44 |

OTHER PUBLICATIONS

Derwent Abstract of CN 101942891 (2011, 5 pages).*

Primary Examiner — Brieann R Johnston
(74) Attorney, Agent, or Firm — Myers Bigel, P.A.

(57) ABSTRACT

An adhesive used in underground applications where vegetation is present wherein the adhesive has been doped with a material or materials that deter the growth properties of adjacent vegetation. The materials can include Zinc, Copper Sulfate, Copper Oxide, as well as sulfates of Zinc, Manganese, and Nickel, in quantities that will repel or deter the advancement of roots and invasive vegetation into fittings and joints in an underground system. The adhesive is used to bond a conduit and a fitting in an air-tight and water tight seal, and the inclusion of the root deterrent material resists invasion of nearby roots into the piping. The root deterring supplements to the adhesive to not degrade the performance of the adhesive and actually repel roots in the vicinity of the materials.

4 Claims, 1 Drawing Sheet

(51) Int. Cl.
  *C09J 121/00* (2006.01)
  *C08K 3/08* (2006.01)
  *C08K 3/30* (2006.01)
  *C08K 3/22* (2006.01)
  *C08K 3/015* (2018.01)
  *F16L 57/00* (2006.01)
  *F16L 58/10* (2006.01)
  *F16L 1/11* (2006.01)

(52) U.S. Cl.
  CPC ........ *C08K 3/30* (2013.01); *C08K 2003/0862* (2013.01); *C08K 2003/0893* (2013.01); *C08K 2003/2248* (2013.01); *C08K 2003/3045* (2013.01)

(56) References Cited

U.S. PATENT DOCUMENTS

| | | | |
|---|---|---|---|
| 5,575,112 | A | 11/1996 | Scheubel |
| 6,440,440 | B1 | 8/2002 | Meerpoel et al. |
| 7,455,851 | B1 * | 11/2008 | Nelson .................. A01N 43/40 424/405 |
| 2005/0152869 | A1 * | 7/2005 | Weed ...................... B05D 7/54 424/78.09 |
| 2006/0246149 | A1 | 11/2006 | Buchholz et al. |
| 2010/0239679 | A1 | 9/2010 | Greene et al. |
| 2010/0260866 | A1 | 10/2010 | Lu |
| 2013/0102469 | A1 | 4/2013 | Tobiason |
| 2013/0236696 | A1 * | 9/2013 | Poole ...................... C23C 24/04 428/148 |
| 2013/0310428 | A1 | 11/2013 | Joseph et al. |

\* cited by examiner

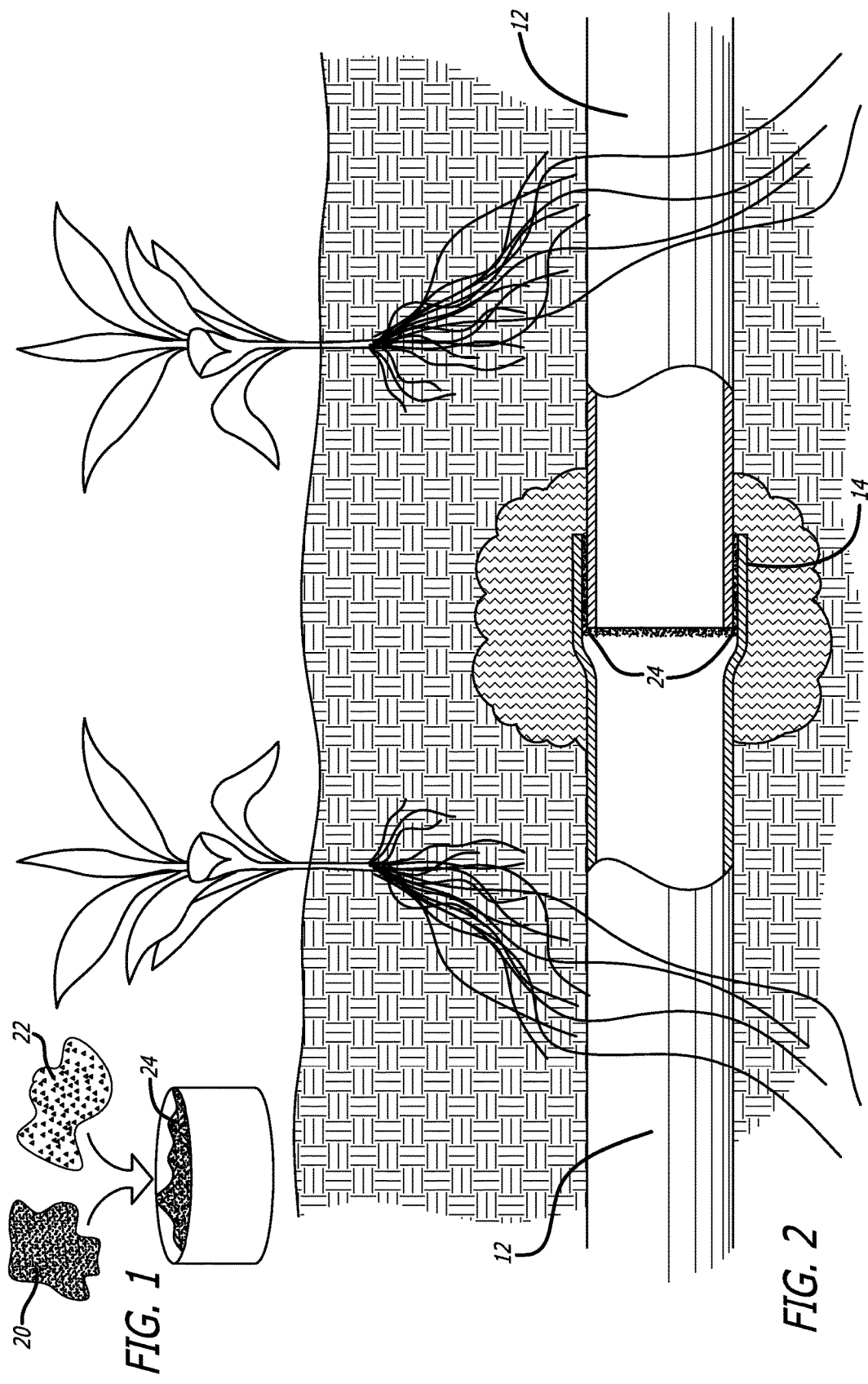

PIPE FITTING ADHESIVE COMPOUND WITH VEGETATION DETERRING PROPERTIES

CROSS-REFERENCES TO RELATED APPLICATION

This application U.S. Ser. No. 14/938,522, filed Nov. 11, 2015, claims priority from U.S. Application No. 62/078,812, filed Nov. 12, 2014, incorporated by reference in its entirety.

BACKGROUND

Irrigation systems and sewer systems are two of many types of underground operations in which fluids are passed through piping to move a type of fluid from one location to another. In irrigation systems and sewer systems, a matrix of conduits are disposed in the soil connected together by fittings, joints, connectors, valves, and other components that establish the pathways for the fluid to navigate from a source to a destination. Many components of current fluid transport systems are made from lightweight plastics such as polyvinyl chloride ("PVC"), polyethylene, HDPE, and Styrene. Where the junctures of two adjacent components are formed, e.g., conduits or fittings, the mating of the two components are typically secured by either a threaded connection or a press fit connection bolstered by an adhesive selected especially for the material(s). Where adhesives are used to bond two mating fluid couplings, they are generally effective at preventing leaks, but the main function is to keep the conduits and fittings fixed together in a working mechanical relationship. Over time, the connection between the adjoining components may slip or adjust due to a variety of external conditions, such as varying loads from the soil shifting, torqueing of the lines, age, wear, and the like, along with internal conditions such as pressure variations, leading to minute separations of the mating components and a small amount of enclosed fluid being released into the adjacent soil. This small amount of fluid is usually not so great as to require that the conduit be replaced or repaired, but moisture in the soil can lead to other problems.

One issue that arises in this situation where a minute leak of water into the soil surrounding the piping acts as an attraction for migration of vegetation to the location of the leak. Small amounts of water in the soil can attract roots of trees, plants, grasses, or the like, which when in proximity with a weakness in the piping can then invade the conduits at the joints through the small separations. This intrusion of vegetation into the conduit, especially at locations where the conduit may be weakened through age or damage, can cause more damage and exacerbate the leaks. Tree roots can also pass into the conduits through cracks at the leaks, clogging the piping if left to grow and expand, and the presence of the roots can also introduce unwanted impurities in the fluid transport system. Roots have been known to destroy an underground piping system and require expensive repairs or even replacement if left untreated. To remove the roots, excavation and manual extraction of the roots are routinely required, which can be both costly and inconvenient.

The use of selected materials in irrigation systems are known to resist intrusion of roots and vegetation. Westman, U.S. Pat. No. 4,647,072 taught a repair sleeve for a pipe fitting that included a coating of copper sulfate to inhibit root growth in the repair fitting. Tobiason, U.S. Patent Publication No. 2013/0102469 taught the use of herbicides to sewer lines to prevent vegetation growth in the lines. Scheubel, U.S. Pat. No. 5,575,112 taught a fabric made of a water-permeable synthetic fibers coated with an inorganic copper compound as part of a method for controlling the growth of plant roots. However, each of these proposals and solutions have drawbacks in the real world that make them impractical to implement and costly or ineffective.

Accordingly, the present invention seeks to address the situation of root invasion into underground piping systems using a growth deterrent in the system's adhesive to repel or deter moisture seeking roots and vegetation near vulnerable or damaged fittings of an underground fluid delivery system from entering the system.

SUMMARY OF THE INVENTION

The present invention is an adhesive to be used in underground or on-ground fluid transport systems, the adhesive being well suited for connections between polymers such as, for example, PVC, as well as other materials. The adhesives of the present invention combine with one or more additives to form a compound that deters the growth properties of adjacent vegetation while not impeding the adhesive's bonding qualities. More particularly, the compound of the present invention has small quantities of Zinc, Copper Sulfate, or Copper Oxide, or other selected sulfates alone or in combination, that will repel or deter the advancement of roots and invasive vegetation into fittings and joints in an underground system. The compound of the present invention bonds adjacent components of a fluid transport system, such as conduits, fittings, and joints, in an air-tight and water tight seal, and the inclusion of the vegetation deterring additive prevents invasion of nearby roots into the piping. The present invention effectively resists root intrusion without biocides and herbicides, and concentrates the root barrier at the location (i.e., the joint) where root damage typically occurs. The root deterring additives to the adhesive do not affect the performance of the adhesive and the invention maintains the integrity of the conduit systems.

BRIEF DESCRIPTION OF THE DRAWING

FIG. 1 is a schematic diagram of an adhesive and additive combined into a compound; and FIG. 2 is an elevation view, partially in cross section, of a conduit in an underground environment and incorporating the compound of FIG. 1 to deter roots and vegetation in adjacent proximity.

DETAILED DESCRIPTION OF THE PREFERRED EMBODIMENT

FIG. 1 illustrates a compound 24 formed by the mixture of an adhesive 20 and a vegetation deterring additive 22 for use in constructing fluid conducting systems.

There are many types of adhesives 20 used in the coupling of polymer conduits, and the present invention is not limited to a specific adhesive. Adhesives are formulated from either natural animal or plant products or a synthetic composition. Natural adhesives are easy to apply and in general are water soluble. Synthetic adhesives are divided into four chemical categories: thermoplastic, thermosetting, elastomeric, and combinations thereof. Thermoplastic adhesives, such as polyvinyl alcohol and acrylics, can be re-softened since the materials do not crosslink upon curing. They require heat or a solvent to create a bond. Thermosetting adhesives, which include epoxies, cannot be heated and re-softened after curing because they do crosslink upon curing. Elastomeric adhesives are based on isoprene rubber or synthetic polymers that combine both elasticity and toughness. Silicone is an example of an elastomeric adhesive.

One preferred adhesive for use in the present invention is rubber cement, which is a solution of unvulcanized (gum) rubber in a solvent. Rubber cement is an opaque liquid that contains pulverized natural or synthetic rubber and a solvent based on hexane or heptane. Grades of rubber cement may contain 70-90% heptane or hexane and 1-15% isopropyl alcohol (isopropanol) or ethyl alcohol (ethanol). Natural rubber comes from the *Hevea brasiliensis* tree originally found in Brazil. To make solid rubber, the tree is tapped and the latex is collected in a small cup, where it coagulates into a lump. This lump, together with the leftover flow and other pieces are collected together and processed at high temperature. This destroys most of the proteins and produces a solid material.

Synthetic rubbers, which are also an important application of the present invention, include neoprene and latex adhesives. Synthetic rubbers are made using various chemical processes. The application determines what types of rubber and solvent are used. Synthetic rubbers can be tailored to the particular use and modified to suspend the root deterring materials while not sacrificing performance.

The present invention utilizes an adhesive such as that set forth above, and incorporates trace to perceptible amounts of a vegetation inhibiting additive 22 to form a vegetation resistant adhesive compound 24. Root inhibiting material means any material that is known to deter the growth of a root into or past the material, forming a barrier against root intrusion. Root inhibiting materials include Zinc, Copper Sulfate, and Copper Oxide, among others. The amount of the root inhibiting material depends on the application, the type of vegetation or trees nearby, and the system for which the adhesive is being used. Investigation has shown that a range of 0.0025:1 to 0.06:1 of root inhibiting material to adhesive will effectively deter root invasion past the joint without deleterious effects on the performance of the adhesive and without problems related to the suspension of the additive within the adhesive. It is to be understood that other ranges may work well with the present invention for different adhesives and materials, and that the present invention is not limited to any particular percentage or range of constituents.

It has also been discovered that combining one or more root inhibiting materials has a synergistic improvement over the contributions of each individual ingredient. Thus, for example, an adhesive doped with Copper Sulfate and Zinc Sulfate works better than either an adhesive with copper sulfate or zinc sulfate alone. Similarly, adhesives with Copper Sulfate with Manganese Sulfate and Copper Sulfate with Nickel Sulfate are more effective than adhesives with the individual materials alone. This synergistic improvement in the use of root inhibiting materials has not been demonstrated in the prior art and is not predicted based on the results of single additives.

The present invention is particularly useful in underground fluid delivery systems where high volumes are moved under relatively low pressures. These situations include drain systems, irrigation systems, water works, sewer/wastewater systems, artificial turf applications, and de-watering environments. The compound of the invention is used as a normal adhesive, applying to the pipes and fittings along mating surfaces after the root inhibiting material has been introduced and suspended in the adhesive. In one preferred embodiment, the compound of adhesive and additive is spread entirely around the interior surface of the bell-shaped female socket and exterior surface of the male section of the connecting pipe to, when cured, form a chemical barrier to deter the surrounding vegetation. The conduits are allowed to dry and the adhesive cures and sets, with the root inhibiting material present throughout the adhesives. The conduits are then laid in the ground, exposed to the soil and the opportunity for encroachment by roots and other vegetation. The presence of the root inhibiting material deters, and often repels, any roots or vegetation that approaches the fittings due to moisture seepage. In this manner, the underground system is protected from costly and troublesome root incursion, and expensive repairs and replacement of the system is avoided.

An example of the environment of the present invention is illustrated in FIG. 2, where an underground conduit 10 includes two pipes 12 connected by an intermediate fitting 14 (which may or may not be part of one of the two pipes 12). The intermediate fitting 14 can be a socket that receives a pipe end in a male/female relationship, or alternatively the fitting may be a separate sleeve that fits over the ends of the two adjacent pipes 12 and locks the pipes together in a mechanical arrangement. In yet other embodiments, the fitting may be any of a variety of joints or couplings including Ts, Ls, Ys, or other pipe fittings used in the connection of fluid transport systems. The pipes 12 and fitting 14 may be manufactured from a variety of different materials, including Polyethylene, High Density Polyethylene, Styrene, PVC, and the like. To further secure the two pipes 12 together using the fitting 14, the compound 24 is applied to mating surfaces to bond the components together in an air-tight and water-tight seal. The compound improves the rigidity of the structure and the coupling of the components by forming a strong joint that is less susceptible to shifting and separation, and prevents or resists seepage and leaks.

The foregoing descriptions and illustration is intended to be exemplary only and not intended to limit the bounds of the present invention. It is understood and recognized that one of ordinary skill in the art would readily appreciate modifications and substitutions to the exemplary embodiments described herein, and the invention is intended to include all such modifications and substitutions. Accordingly, the present invention is not limited by any description or illustration, but rather bound only be the words of the appended claims, using the ordinary and customary meaning of such words in light of the foregoing.

I claim:

1. An adhesive compound comprising:
   a base adhesive comprising unvulcanized rubber in a solvent selected from hexane and heptane, and a secondary constituent selected from isopropanol and ethanol; and
   an additive including nickel and zinc incorporated into the base adhesive to form a compound, the additive selected for its vegetation deterring properties;
   wherein the additive to base adhesive is in the range of 0.0025:1 to 0.06:1.

2. The adhesive of claim 1, wherein the additive includes manganese.

3. The adhesive of claim 1, wherein the additive includes copper sulfate.

4. The adhesive of claim 1, wherein the additive includes copper oxide.

* * * * *